United States Patent [19]

Kissel et al.

[11] Patent Number: 4,863,740
[45] Date of Patent: Sep. 5, 1989

[54] INTERLEUKIN THERAPY

[75] Inventors: Thomas Kissel; Jürg Reinhardt, both of Ehrenkirchen, Fed. Rep. of Germany; Henriette Schrank, Riehen, Switzerland

[73] Assignee: Sandoz Ltd., Basel, Switzerland

[21] Appl. No.: 193,423

[22] Filed: May 12, 1988

Related U.S. Application Data

[63] Continuation of Ser. No. 896,551, Aug. 14, 1986, abandoned, which is a continuation of Ser. No. 721,316, Apr. 9, 1985, abandoned.

[30] Foreign Application Priority Data

| Apr. 9, 1984 | [GB] | United Kingdom | 8409125 |
| Apr. 9, 1984 | [GB] | United Kingdom | 8409126 |
| Apr. 9, 1984 | [GB] | United Kingdom | 8409127 |
| Apr. 9, 1984 | [GB] | United Kingdom | 8409128 |
| Aug. 10, 1984 | [GB] | United Kingdom | 8420381 |
| Sep. 19, 1984 | [GB] | United Kingdom | 8423700 |
| Sep. 19, 1984 | [GB] | United Kingdom | 8423701 |

[51] Int. Cl.$^4$ .................... A61K 31/335; A61K 39/00
[52] U.S. Cl. ..................................... 424/450; 424/85.1
[58] Field of Search .................. 424/417, 450, 85.2, 424/85.1; 436/829

[56] References Cited

U.S. PATENT DOCUMENTS

| 4,016,100 | 4/1977 | Suzuki et al. | 252/316 |
| 4,235,871 | 11/1980 | Papahadsopoulous et al. | 424/19 |
| 4,522,803 | 6/1985 | Lenk et al. | 424/1.1 |
| 4,619,794 | 10/1986 | Hauser et al. | 264/4.1 |
| 4,764,359 | 8/1988 | Lemelson | 424/450 |

FOREIGN PATENT DOCUMENTS

| 109861 | 5/1984 | European Pat. Off. |
| 132359 | 1/1985 | European Pat. Off. |

OTHER PUBLICATIONS

Ostro. "Liposomes", Marcel Dekker, Inc., pp. 73, 242, 243 and 315.

Primary Examiner—Douglas W. Robinson
Assistant Examiner—R. Kearse
Attorney, Agent, or Firm—Gerald D. Sharkin; Richard E. Vila

[57] ABSTRACT

Interleukin-2 liposomes are advantageous sustained release formulations.

15 Claims, No Drawings

INTERLEUKIN THERAPY

This is a continuation of application Ser. No. 896,551, filed Aug. 14, 1986, now abandoned, which in turn is a continuation of application Ser. No. 721,316, filed Apr. 9, 1985, now abandoned.

This invention relates to interleukin therapy. Interleukin-2 (hereinafter IL-2) is a naturally occurring protein factor first discovered in 1976. It is produced from T-cells activated by an antigen or lectin and is a factor essential for the proliferation of T-cells. IL-2's of various structures have been isolated from a number of animal species, e.g. mouse, primate such as the gibbon, ape, and human. Human and other IL-2's have been purified from various sources such as peripheral blood lymphocytes, tonsilar lymphocytes, spleen lymphocytes, T-cell leukemia and T-cell hybridoma cultures.

As indicated above IL-2 is a factor essential for the proliferation of T-cells, themselves intimately involved in the body's immune response mechanisms. IL-2 is anticipated to have therapeutic potential of immense proportions. In particular, it may have value in the therapy of tumours since it leads to proliferation of antigen specific T-cells e.g. against tumour antigens and these T-cells can inhibit tumour growth. It is also known that IL-2 induces production of gamma-interferon and activates natural killer cells. It is also expected that IL-2 will have a variety of applications against immunological disorders, such as neoplastic diseases, bacterial or viral infections, immune deficient diseases, auto-immune diseases etc (see B. Papermaster et al, Adv. Immunopharm. (1980) 507).

As with other naturally occurring products such as the interferons, before the advent of genetic engineering, IL-2 was available in small quantities only.

However, following methodology similar to that previously published for other proteins (e.g. gamma-interferon) the structure determination and expression of a cloned gene for human IL-2 was effected (see S. Taniguchi et al, Nature (1983) 302, p. 305–310 and European Patent Publication No. 91539 the contents of both which are incorporated by reference. This particular IL-2 is referred to hereinafter as known IL-2.

On the basis of the nucleotide coding sequence the amino acid sequence of the human IL-2 polypeptide, namely that comprising the amino acids numbered 1 to 153 in FIG. 3a of the above Nature article, was deduced. It was postulated, however, that the first 20 animo acids of this sequence could be cleaved on transmembrane transport. The mature human IL-2 would then consist of 133 amino acids beginning with the Ala at position 21.

This structure of human IL-2 has since been confirmed in our and other laboratories.

It is also possible by using recombinant DNA techniques to produce IL-2's of different structures. For example, modifications of the human IL-2 polypeptide having one or more amino acids absent or replaced by other amino acids, e.g. as described in the above mentioned European Patent Publication, in particular pages 23 to 25 thereof, may be produced by correspondingly modifying the human IL-2 gene. For example, if desired Cysteine residues may be replaced by other amino acids, e.g. serine, as described in Cetus European Patent Publication No. 109748 and Belgium Patent 898016, e.g. IL-2-serine-125, the contents of which are hereby incorporated by reference.

Further examples of such interleukins are disclosed in PCT patent publication WO 85/00817, the contents of which are incorporated herein by reference. These include IL-2 Gln-26, IL-2 Phe-121, and IL-2 Stop 121.

Furthermore, IL-2's from different sources such as the gibbon ape may be produced by recombinant DNA techniques and modification of these may also be produced in similar manner. Furthermore, IL-2's may, as indicated, be isolated (albeit in relatively small quantities) from natural sources and may differ from the products produced by recombinant DNA technology in for example glycosylation. Moreover, allele variantes may be produced.

IL-2's may also be produced by cultivating human cells, e.g. in the presence of an inducer. Examples are IL-2 A-1, IL-2 A-2, IL-2 B-1, IL-2 B-2 as defined in Danish Patent Application No. 3317/84 and European Patent Publication No. 132359, the contents of which are incorporated herein by reference.

By "interleukin" as used hereinafter is meant any polypeptide, including but not limited to those described above, whether isolated from natural sources or produced by a synthetic or biosynthetic method and which has IL-2 activity. In accordance with the present invention, the preferred interleukin is human IL-2 or a modification thereof, preferably as produced by recombinant DNA methods. Trials so far carried out with interleukin have been by injection, e.g. intravenously. These have shown for example that human IL-2 has a very short half-life of under 5 minutes. There is clearly a need for a sustained release parenteral form of interleukin providing a sufficiently long duration of action, however, up to now little has been published on specific galenic formulations on interleukins.

Furthermore, trials carried out in our laboratories have shown that interleukin may be incorporated into liposomal forms, which on administration, e.g. intravenous administration, still show IL-2 activity. Furthermore, the liposomes of the present invention have a prolonged half-life, are passively targetted into the spleen, lung, bone marrow or lymph nodes.

The present invention accordingly provides interleukin - containing liposomes.

Liposomes according to the invention may be prepared by encapsulating an interleukin in a liposome forming material.

Liposomes are completely closed bilayer membranes containing an aqueous phase with the interleukin. The interleukin may be in the aqueous phase and/or in the membrane. They may be in the form of a unilamellar vesicle or a oligoor multi-lamellar vesicle in the form of concentric membrane bilayers each separated from one another by a layer of water.

They may be made by variety of different methods -see F. Szoka and D. Papahadjopoulos, "Liposomes and their uses in biology and medicine" Ann.N.Y.Acad.Sci. 308, 1-462, (1978); R. L. Juliano & D. Layton, "Liposomes as a drug delivery system" in Drug delivery systems p. 189–236, Oxford University Press, Inc., New York, 1980, whose disclosure is incorporated by reference herein, but the method of the invention is preferred as it provide liposomes which have particularly interesting properties. Thus the liposomes produced by this method are especially stable, e.g. against leakage of interleukin and the method of the invention is suitable for commercial production.

The liposomes may be made from a variety of lipids capable of forming vesicle walls. Preferred lipids are phospholipids such as natural lecithin (e.g. egg or soyabean lecithin), synthetic lecithins, kephalines and sphingomyelins. Alternatively, other phosphatidylcholines, phosphatidic acids, lysophosphatidylcholines, sphingolipids, phosphatidylglycerol, cardiolipins, glycolipids, gangliosides and cerebrosides may be used.

Examples of lecithins includes EPIKURONS available from Lucas Meyer, Hamburg 28, W. Germany. One example contains the following phospholipid content: Phosphatidyl choline 44–7%, Phosphatidylethanolamine 22–25%, Phosphatidyl inosit 0–2%, fatty acid content: saturated-palmitic acid 9–11%, stearic acid 2–4%, unsaturated: linoleic acid 63–67%, linolenic acid 5–8%, oleic acid 14–18%, known as EPIKURON 145 V. An alternative example contains greater than 95% phoslatidyl choline e.g. 95–98% and predominantly unsaturated acids, e.g. oleic acid 10–12%, linoleic acid 62–65%, linoleic acid 5–6%, as well as saturated acids, e.g. palmitic acid 15–17%, stearic acid 3–4%, such as EPIKURON 200.

It is preferred to have a high content of unsaturated acids. If desired there may be used a lecithin with a high content of saturated acids, e.g. stearic acid, and phosphatidyl choline 95% or greater, e.g. SOJA PHOSPHI-TID NC 95 or pure equivalents suitable for pharmaceutical use and available e.g. from NATTERMANN CHEMIE GmbH, KOELN, W. Germany.

Synthetic phospholipids may contain altered aliphatic portions such as hydroxyl groups, branched carbon chains, cycloderivatives, aromatic derivatives, ethers, amides, polyunsaturated derivatives, halogenated derivatives or altered hydrophilic portions containing carbohydrate, glycol, phosphate, phosphonate, quaternary amine, sulfate, sulfonate, carboxy, amine, sulfhydryl and imidazole groups, e.g. as in dimyristoyl-, dipalmitoyl- or distearoyl-phosphatocholine derivatives.

If desired in the final liposome the bilayer may contain, e.g. up to 50 (mole) percent of, other lipids, e.g. steroids such as cholesterol.

Preferably in the final liposome a steroid such as cholesterol is present. Suitable weight ratios of phospholiped to steroid may be from 6:1 to 1:1.

If desired the bilayer may comprise a lecithin, kephaline or sphingomyelin containing up to 10 (mole) percent of an additive to increase incorporation, e.g. anionic compounds such as acids, e.g. dicetyl phsophate, phosphatidic acid, sodium taurocholate, phosphatidyl serine (Merck) or cationic compounds e.g. amines such as stearylamine. It is preferred to use phosphatidylserine (obtainable e.g. from Merck, W. Germany).

When the lipid contains extra excipients it may be preferred to evaporate a solution of the lipid and excipients e.g. in methylene chloride in a reaction vessel to form a lipid film on the vessel surface before the lipid is mixed with the interleukin.

The liposomes may be produced by well-known techniques, e.g. by irradiation e.g. ultrasonic sonification, using mild conditions to prevent breakdown of the interleukin. Homogenous mixtures of lipids may be produced by forming a solution of lipid, e.g. lecithin and cholesterol in a suitable organic solvent, e.g. chloroform. The solution in a reaction vessel is then evaporated to produce a lipid film.

The liposomes may be isolated and sterilized in conventional manner.

In the resultant liposomes according to the invention the concentration of interleukin is preferably from about 5 to about 500 microgram/milliliter of aqueous phase, preferably 20 to 200 microgram/milliliter.

The lipid concentration is preferably from about 1 to about 200 mg/ml of aqueous phase, especially 10 to 100 mg/ml.

The average diameter of the liposomes for further use is preferably from about 25 nanometers to 20 microns, preferably from 100 to 500 nanometers.

The final liposomes are preferably storred at low temperatures e.g. $-20°$ C. to $+5°$ C.

In order to improve their storage the liposomes according to the invention may be lyophilized to a dry powder, e.g. by freeze-drying using for example mannitol, sucrose, polyvinylpyrrolidone or gelatin as carrier material. This may be effected under the same conditions for freeze-drying indicated below with respect to step (Ab). Before use they may be reconstituted by the addition of sterile water. They may then be mixed with systems appropriate for, for example, intravenous injection or infusion.

The purity of the liposomes may be determined by conventional analytical techniques.

An anti-oxidant may if desired by present up to e.g. 1% preferably 0.1% of the lipid, in the resultant liposomes. Preferred anti-oxidants include Vitamin E (tocopherol acetate), Vitamin C palmitate and BHT (butylated hydroxytoluene).

Other stabilizers for the interleukin may be present, e.g. sugar, e.g. mannitol, arabinose, sorbitol, or sucrose, albumins e.g. human serine albumin etc. These may be incorporated into the buffer before liposome formation. Preferably they are present in up to 20% by mole weight of the lipid in the resultant liposome.

A preferred process for liposome formation is the following process (a) which comprises (Aa) forming a solution of an interleukin and a lipid in an organic solvent, (Ab) removing the solvent from the solution to give a residue, (Ac) suspending the residue in a solution of a buffer, (Ad) subjecting the suspension to agitation and homogenization until liposomes are produced, and (Ae) isolating the liposomes.

In step (Aa) the term "solution" covers "pseudo" solutions like emulsions, However, it is preferred to produce a uniform, clear solution. Any solvent system may be used which will dissolve or solubilize the interleukin and the lipid. The system may be a single solvent or a mixture of solvents. It may contain up to e.g. 15% water. If desired a surfactant may be present. The solvent system may comprise any appropriate organic solvent which can be removed from the lipid by evaporation. A wide variety of ethers, such as diethyl ether, and diisopropyl ether, ester such as ethyl acetate, alcohols such as methanol and tert-butanol, and halogenated hydrocarbons such as methylene chloride and chloroform may be used. If desired acetic acid may be present. It is preferred to use diethylether, methylene chloride or tert-butanol.

We have found that tert-butanol is preferred when high vacuum is used, and methylene chloride when a low vacuum is used, in step (Ab).

In step (Ab) the solvent may be removed by many conventional means bearing in mind that the sensitivity of the interleukin. Preferred means comprise evaporation under a low vacuum, e.g. 10 to 50 mm Hg, or freeze-drying under a high vacuum, e.g. at below 5 mm Hg, e.g. 0.1 mm Hg.

We have found freeze-drying espeically preferred. Suitably the step is effected at a temperature below room temperature, and the vacuum and temperature controlled such that the mixture being evaporated is about 1-3 degrees Centigrade cooler than the surroundings. Such control may be effected in conventional manner. A typical program for freeze-drying starts at about −60° C. and increases to −15° C. over 12 hours. The temperature is then increased to +10° C. and maintained for 2 hours.

In step (Ac) the buffer used is preferably a phosphate buffer, e.g. of pH 4–7, e.g. 5–6.5. Preferably the aqueous phase is hypotonic, e.g. less than 300 mosmol/liter, especially less than 290 mosmol/liter. The resultant suspension preferably contains about 0.001 to about 0.2 g lipid per ml.

In step (Ad) homogenisation may be provided by ultrasonic radiation. Suitable frequencies of such radiation may be for example from 30 to 80 kHz. A typical power is from 200 to 400 Watts for about 10 ml of mixture being homogenized or agitated. Naturally it is preferred to have the mixture being homogenized separated from any titanium or other metal associated with the ultrasonic radiation generator to avoid contamination by the metal.

The temperature is preferably from about 10° to 70° C. Room temperature is preferred for unsaturated lipids and 60°–70° C. for saturated lipids.

During this stage an emulsion of liposomes with agglomerates may form.

If desired the ultrasonic radiation may be followed by agitation by a high speed mechanical stirrer at e.g. 10,000 to 27,000 rpm. It is preferred, however, to omit this stage, and have agitation provided also by ultrasonic radiation under the same conditions as for homogenization.

In step (Ae) the liposomes according to the invention may be isolated according to conventional techniques, e.g. by ultrafiltration, centrifugation, ion-exchange or gel chromatography, dialysis etc. The liposomes may be filtered and sterilized through a filter with suitably small openings, e.g. 0.1 to 1 micron. If desired the filtration may be effected above the phase transition point of the lipid, e.g. from 30° to 70° C. Preferably the liposomes are isolated by high speed centrifugation, e.g. at 10,000–20,000 g.

An example of process (a) is (a′a) mixing a hydrophilic solution of a interleukin with a lipid in an organic solvent, (a′b) removing the water and organic solvent by evaporation, (a′c) taking up the residue in a buffer solution of a pH 4–7 to form a suspension (a′d) subjecting the suspension to ultrasonic radiation to form liposomes, and (a′e) isolating the liposomes.

Another example of process (a) is (a′a) mixing a hydrophilic solution of an interleukin with lipid in an organic solvent, (a′b) freeze-drying the mixture to give a lyophilisate, (a′c) suspending the freeze-drying mixture in a solution of a buffer (pH 4–7), (a′d) subjecting the solution to agitation until liposomes and/or agglomerates are produced, (a′e) homogenization the mixture by mechanical means, and (a′f) isolating the liposomes.

These precesses may be effected in analogous manner to process (a).

In another aspect the invention provides a process (b) for producing interleukin-containing liposomes which comprises (ba) mixing an aqueous based solution of an interleukin and an organic solution of lipid, (bb) irridating the mixture ultrasonically until some liposomes and/or agglomerates are formed, and (bc) recovering liposomes from the mixture, e.g. by (bi) removing organic solvent from the mixture to form a gel - like intermediate phase, and (bii) converting the gel - like intermediate phase into liposomes.

In step (ba) the term "solution" covers "pseudo" solutions like emulsions. However, it is preferred to produce a uniform, clear solution. Any solvent system may be used which will dissolve or solubilize the lipid. The system may be a single solvent or a mixture of solvents. It may contain up to e.g. 15% water. If desired, a survactant may be present.

The solvent system may comprise any appropriate organic solvent which can be removed from the lipid by evaporation. A wide variety of ethers, such as diethyl ether, and diisopropyl ether, esters such as ethyl acetate, alcohols such as methanol and tert-butanol, and halogenated hydrocarbons such as methylene chloride and chloroform may be used.

If desired acetic acid may be present. It is preferred to use tert-butanol or preferably diethyl ether or methylene chloride.

The interleukin may be dissolved in water or preferably an aqueous buffer system of pH 4–7.4, e.g. 5 to 6.5.

Preferably the aqueous buffer is hypotonic, e.g. less than 300 mosmol/liter, especially less than 290 mosmol/litre. The resultant mixture preferably contains about 0.001 to about 0.2 g lipid per ml.

In step (bb) irradiation may be provided by ultrasonic radiation. Suitable frequencies of such radiation may be for example from 30 to 80 kHz. A typical power is from 200 to 400 Watts for each 10 ml of mixture being irradiated. Naturally it is preferred to have the mixture being irradiated separated from any titanium or other metal associated with the ultrasonic radiation generator to avoid contamination by the metal.

The temperature is preferably from about 10° to 70° C. Room temperature is preferred for unsaturated lipids and 60°–70° C. for saturated lipids.

During this stage an emulsion of liposomes with agglomerates may form.

The liposomes may be recovered in conventional manner, and steps taken to optimise their yield.

In step (i), the organic solvent is conveniently removed under a low vaccum, e.g. from 10 to 600 mm Hg, whilst still retaining most of the aqueous phase. Preferably low temperatures are used, e.g. room temperature or slightly elevated temperatures e.g. to 45° C.

In step (ii), the resultant gel like intermediate phase may be treated with water, optionally a buffer solution as described above to produce the liposomes.

In another aspect the invention provides a process (c) for producing interleukin-containing liposomes which comprises (ca) mixing a interleukin, a aqueous-based buffer at pH 4–8, and lipid in an organic solvent, (cb) radiating the resultant suspension ultrasonically to form liposomes or agglomerates, and (cc) recovering liposomes from the mixture e.g. by (ci) evaporating the solvent from the mixture, e.g. by a gel - like intermediate phase, and
(cii) converting the gel - like intermediate phase into liposomes.

In step (ca) the term "solvent" covers "pseudo" solutions like emulsions. However, it is preferred to produce a uniform, clear solution. Any solvent system may be used which will dissolve or solubilize the lipid. The system may be a single solvent or a mixture of solvents. It may contain up to e.g. 15% water. If desired a surfactant may be present. The solvent system may comprise any appropriate organic solvent which can be removed from the lipid by evaporation.

A wide variety of ethers, such as diethyl ether, and diisopropyl ether, esters such as ethyl acetate, alcohols such as methanol and tert-butanol, and halogenated hydrocarbons such as methylene chloride and chloroform may be used. If desired acetic acid may be present. It is preferred to use diethylether, methylene chloride or tert-butanol.

The interleukin may be used in powder form, e.g. with a particle size of a conveniently maximum particle size of 60 microns in diameter.

In step (ca) the buffer used is preferably a phosphate buffer, e.g. of pH 4–7.4, such as 4 to 7, e.g. 5–6.5. Preferably the aqueous phase is hypotonic, e.g. less than 300 mosmol/liter, especially less than 290 mosmol/liter. The resultant suspension preferably contains about 0.001 to about 0.2 g lipid per ml.

In step (cb) radiation may be provided by ultrasonic radiation. Suitable frequencies of such radiation may be for example from 30 to 80 kHz. A typical power is from 200 to 400 Watts for about 10 ml of mixture being radiated. Naturally it is preferred to have the mixture beine radiated separated from any titanium or other metal associated with the ultrasonic radiation generator to avoid contamination by the metal.

The temperature is preferably from about 10° to 70° C. Room temperature is preferred for unsaturated lipids and 60°–70° C. for saturated lipids.

During this stage an emulsion of liposomes with agglomerates may form.

The liposomes may be recovered in conventional manner, and steps taken to optimise yields of liposomes. In step (ci), the organic solvent is conveniently removed under a low vacuum, e.g. effected by a water pump at for example from 10 to 600 mm Hg, whilst still retaining most of the aqueous phase. Preferably low temperatures are used, e.g. room temperatures or slightly elevated temperatures, e.g. to 45° C.

In step (cii), the resultant gel - like intermediate phase may be treated with water, optionally a buffer solution as described above to produce the liposomes.

A suspension may form. If desired further evaporation may be effected to remove residue traces of organic solvent and acid liposome formation.

The liposomes according to the invention may be further isolated according to conventional techniques, e.g. as in process step (ae).

The purity of the liposomes may be determined by conventional techniques.

To determine the incorporation of interleukin in the liposomes, the prepurification crude mixture may be diluted and centrifuged e.g. for 3 to 24 hours and the amount of interleukin in the supernatant liquor determined. The residueal interleukin is then taken to be incorporated in the liposomal sediment.

Additionally, the incorporation of interleukin in the purified liposomes may be determined by standard high performance liquid chromatographic techniques as described in the Examples hereinafter.

The distribution of the liposomes according to the invention after administration may also be followed by conventional pharmacokinetic techniques, e.g. in animal tests. Radioactive interleukin is made by reacting iodine-125 with interleukin or by producing the interleukin from amino acids which are radioactively labelled, e.g. with sulphur 35. This interleukin is incorporated into liposomes, which are produced from radioactively labelled lipids, e.g. with carbon-14, and injected into mice. After 1 hour the mice are sacrificed and the amount of and type of radio-activity in each of the organs e.g. spleen, is measured.

The liposomes of the invention may be used in a variety of applications known for interleukins. These applications include use to promote growth of animal cells in culture and other in vitro applications and also include therapeutic use in treating a variety of conditions.

In one test hereinafter referred to as the bioassay test a interleukin bioassay is made based on the interleukin concentration dependent stimulation of proliferation of a mouse-T-lymphocyte cell series (CTLL cells) (see S. Gillis et al. J. Immunol. (1978), 120, p. 2027–2032).

T-cells of a interleukin-dependent cell-culture were washed to remove IL-2 and were treated with liposomes according to the invention, and incubated in an IL-2 free medium. The test cells were then subjected to a conventional series dilution test (dilution medium RPMI-1640, supplemented with 10% fetal calves serum). The proliferation of the cells after 24 hours incubation measured against increasing liposome concentration. For each dilution $2.10^5$ cells were used.

The proliferation ismeasured through the incorporation of [$^3$H]-thymidine or the photometric MTT test (MTT = (3'(4,5-Dimethylthiazol-2-yl)-2,5-diphenyltetrazolinebromide). The yellow MTT of the living cells in converted into the corresponding dark blue formazan which is measured after dissolution in acidic isopropanol spectrophotochemically.

The dilution of a sample giving 50% of the maximum proliferation rate is measured. The activity of the liposomes according to the invention is about 1.2 to 20 times less than that of pure interleukin. Preferably the liposomes are used which have an activity of greater than 1.3 ng/ml in the above test.

The activity may also be confirmed in standard in vivo tests for IL-2 activity, e.g. in mice with suppressed T-lymphocyte cells e.g. nude mice. In one test such mice are produced by daily administration of 90 mg/kg cyclosporin A whereupon after immunisation with sheep erythrocytes (SRC) the number of specific antibody cells (PFC) in the spleen according to the Jerne Plaque-forming cell assay is reduced by 80 to 97%. After i.v. injection of the antigen the mice are divided up into groups (6–7 animals per group) and given IL-2 preparations in doses containing about 2 to 5 micrograms of IL-2 by sub-cutaneous or preferably i.v. injection twice daily over 5 days. The revival of the immunity of the animals was determined by measuring the number of specific antibody cells in the spleen according to the Jerne test. The activity of the liposomes of the invention is of the same order as the unencapsulated interleukin.

It is preferred to use the liposomes of the invention in therapeutic applications of particular interest based on the recognized immuno-regulatory properties of interleukins, e.g. as mentioned on page 1 of this specification, in particular their use in treatment of conditions due to immunodeficiencies such as the severe combined immunodeficiency syndrome (SCIDS), the acquired immunodeficiency syndrome (AIDS), immunodeficiency states of old age and congenital immunodeficiency. However, the interleukin may also be used as an antimyotic agent in the treatment of various viral diseases such as cytomegalovirus infections and Herpes virus infections and in the treatment of bacterial infections such as Tuberculosis and Leprosis. Dosages required for such therapeutic use of liposomes will vary depending upon known factors such as the condition being treated, the severity of the condition and potency and amount of the interleukin incorporated, and the like.

However, satisfactory results may be generally obtained when administered to mammals, e.g. human patients, in daily dosages of interleukin ranging from 0.1 μg to 30 μg/kilogram of body weight. Intravenous administration in a suitable sterile vehicle is generally preferred.

Among the wide variety of particular uses of interleukin based on its ability to promote T-cell growth in culture are those which find application in diagnostics and in assisting therapeutic treatments. Use in diagnostics is based on the known ability to detect the presence of certain diseases by determining the extent of T-lymphocite growth in vitro after addition of the interleukin, using the uptake of radioactive thymidine in the cells as a measure. In assisting therapeutic treatments, such as anti-tumor treatment, the interleukin may be used to promote in vitro the growth of T-lymphocytes obtained from the patient or other compatible donor, and the resulting proliferate lymphocytes then reinfused to the patient to assist in combatting the condition. In general, the amount of interleukin to be used to support T-cell growth in culture and other in vitro applications may be generally determined from literature accounts of its activity and of its comparison to human interleukin in such ystems, and may be optimized for particular situations by routine investigations.

The following examples illustrate the invention: As used hereinafter "lecithin" refers to soya-bean lecithin.

Ultrasonic radiation is at 50 KHz and 350 W, unless otherwise stated.

PROCESS A

EXAMPLE A1

Preparation of liposomes 2 mg of human IL-2 are dissolved in 1 ml of acetic acid. 1 gram of purified lecithin is separately dissolved in 5 ml tert-butanol. The two solutions are mixed together and freeze dried at −30° C. to give a lyophilizate. The lyophilizate is taken up with 0.05M phosphate buffer (pH 5) to 10 ml giving a suspension.

The suspension is subjected to ultrasonic radiation in a bath for 5 minutes. The suspension then is homogenized for 15 minutes with a high speed stirrer at about 15,000 r.p.m. (Type Polytron Type 10-30) under nitrogen. The liposome solution is then pressed through a sterile filter (0.2 microns) at a temperature greater than the phasetransition point of the lecithin, e.g. 20° C. The resultant liposomal solution is then lyophilised.

If desired the high speed stirrer step may be omitted and the radiation continued for 15 minutes, and/or the liposomes isolated by centrifugation.

ANALYSIS OF LIPOSOMES

The liposomes of the invention may be analysed using conventional reversed phase high performance liquid chromatographic (HPLC) techniques.

It is preferred to use wide pore (ca 300 angstroms) spherical C-8 hydrocarbon support material, 10 microns (e.g. column RP 300 Aquapore 20×4.6 mm) available from Browlee Laboratories Inc. USA).

A preferred eluant system is a water/acetonitrile gradient with 0.1% trifluoroacetic acid, e.g. using two eluant systems.

System A: 50% acetonitrile in H$_2$O (+0.1% trifluoroacetic acid)

System B: 70% acetonitrile in H$_2$O (+0.1% trifluoroacetic acid).

Typical flow rates are 3 ml/minute and with a gradient of system 100 percent A to 100 percent system B over 10 minutes. Under such preferred conditions human IL-2 is eluted with a retention time of about 7.5 minutes and the amount of interleukin can be obtained by integration of the peak in conventional manner.

The liposomes of the invention are pre-treated before HPLC (i) by dilution with acetate buffer of pH 2.5 to 4 after which the lipsome material breaks down on the HPLC column releasing the interleukin, (ii) by exhaustive removal of liposome excipient from the interleukin incorporated in the liposomes, e.g. water and methanol/methylene chloride to remove phospholipids and then injection of the resultant aqueous solution containing interleukin, (iii) by column switching technique where the liposomes excipients from the interleukin incorporated in the liposomes of the invention are separated on a cation exchanger. Afterwards interleukin is eluted from the cation ion exchanger to a reversed phase column where it is chromatographed in the usual way. A suitable cation ion exchanger column has 30×4.6 mm in size, packed with 10 μm support (f.e. SC×10 available from Browlee Laboratories Inc. USA).

The liposomes are found to incorporate about 50% of the human IL-2.

ACTIVITY AND UTILITY

The liposomes are found to show the same order of activity as human IL-2 itself in the above-mentioned bioassay test.

EXAMPLE A2

Preparation of Lyposomes (V3)

0.5 mg human IL-2 are dissolved in 1 ml acetic acid. 500 mg of lecithin (EPIKURON 145 V) is separately dissolved in 50 ml t-butanol. The two solutions are mixed together and freeze dried at −15° C. over about 16 hours to give a lyophilizate. The lyophilizate is taken up with 0.05M phosphate buffer (pH 6.5) to 10 ml giving a suspension.

The suspension is subjected to ultrasonic radiation in a bath for 5 minutes at room temperature (ca 20° C.). The suspension is then homogenized for 10 minutes with a high speed stirrer at about 15.000 r.p.m. (Type Polytron PT 15) at room temperature.

The liposomes are isolated by centrifugation at 150,000 g at 4° C. for 4 hours.

EXAMPLE A3

Preparation of Liposomes

Examples A2 is repeated with ultrasonic radiation and high speed stirrer homogenization at 70° C. instead of room temperature. The lecithin used was Soja phosphatid NC 95H. Centrifugation time was 2 hours.

EXAMPLE A4

Preparation of Liposomes 0.5 mg of human IL-2, 450 mg lecithin (Epikuron 145 V) and 50 mg phosphatidylserine are mixed together in 10 ml tert-butanol and irradiated for 10 minutes at room temperature to form a solution. The solution is freeze-dried at −40° C. over about 18 hours to form a lyophilisate.

The lyophilisate is taken up with 0.05M phosphate buffer (pH 6.3) to 10 ml giving a suspension. The suspension is subjected to ultrasonic irradiation in a bath for 10 minutes at room temperature (20° C.) and then homogenised as in Example 2 for 10 minutes. The liposomes are isolated by centrifugation at 150,000 g at 4° C. for 4 hours.

EXAMPLE A5

Preparation of liposomes

Example A4 is repeated using 500 mg of lecithin in place of 450 mg lecithin and 50 mg phosphatidylserine.

EXAMPLE A6

Preparation of liposomes

Example A4 is repeated using 425 mg lecithin and 75 mg cholesterin in place of 450 mg lecithin and 50 mg phosphatidylserine.

EXAMPLE A7

Preparation of liposomes

Example A2 is repeated without the high speed stirring step. Ultrasonic irradiation continued for 15 minutes.

EXAMPLE A8

Preparation of liposomes

Example A 3-6 are each repeated without the high speed stirring step.

ANALYSIS OF LIPOSOMES

Supernantant liquid

The supernatant liquid after centrifugation is analysed by reversed phase high performance liquid chromatographic techniques as described above and contain less than 10% of the original human IL-2.

Biological activity

The liposomes are analysed according to the series dilution test on the incorporation of $^3$[H]-thymidine in IL-2 dependent CTLL-(16) cells in the test described above (S. Gilles et al). The concentration of IL-2 which produces 50% of the maximal growth of $10^4$ cells after 24 hours is measured immediately after preparation (Value A in $\mu$g/ml). In this test the substance human IL-2 itself used as starting material for liposome formation had a value of 0.2 $\mu$g/ml.

Results

| Example | A° (ng/ml) | $A^2$ (ng/ml) | $A^4$ (ng/ml)* |
|---|---|---|---|
| A2 | 0.2 | 0.7 | 3.2 |
| A3 | 9.5 | 8.4 | nt |
| A4 | 0.7 | nt | nt |
| A5 | 2.6 | nt | nt |
| A6 | 1.6 | nt | nt |
| A7** | 1.0 | nt | nt |

*storage after 4 weeks at 4° C.
**initial IL-2 charge 0.8 ng/ml activity
nt = not tested In the above in vivo test the following results were obtained with a stored batch of the Example A2 liposomes having an in vitro activity in the above test of 1.7 ng/ml:

| | Dose in micro grams | PFC in spleen | Activity relative to activity of control |
|---|---|---|---|
| Immunized non-suppressed mouse (Control) | — | 167,000 | 100% |
| Suppressed mouse | — | 28,000 | 17% |
| IL-2 substance | 5 | 111,000 | 66% |
| Liposomes | 5 | 96,700 | 58% |
| IL-2 substance | 2 | 96,700 | 58% |
| Liposomes | 2 | 87,100 | 52% |

EXAMPLE A9

Preparation of Liposomes 0.5 mg human IL-2 is dissolved in 1 ml acetic acid and the solution is added to a solution of 500 mg lecithin (Epikuron 145 V) in 50 ml methylene chloride.

The mixture is evaporated in a rotary evaporator at 30° C. under a vacuum of 10 to 50 mm Hg for 1 hour and then at 50° C. for 3 hours to give a lipid film. The film is dispersed in 10 ml (0.02M) phosphate buffer at pH 5. The dispersion is then irradiated in an ultrasonic bath for 30 minutes at room temperature (20° C.) to form liposomes.

The liposomes are isolated by centrifugation at 15,000 g at 40° C. for 4 hours.

EXAMPLE A10

Preparation of Liposomes

Example 9 is repeated with ultrasonic irradiation at 70° C. instead of room temperature. The lecithin used was Soja phosphatic NC 95 H. The centrifugation is effected for 2 hours.

ANALYSIS OF LIPOSOMES

Analogues to analysis effected for EXAMPLE A4

| Results Example | A° (ng/ml) | $A^2$ (ng/ml) |
|---|---|---|
| A9 | 0.8 | 0.9 |
| A10 | 2.5 | 3.5 |

PROCESS B

EXAMPLE B1

Preparation of Liposomes 100 mg of lecithin are dissolved in 5 ml methylene chloride and placed in a round bottomed flask. An aqueous solution of 0.2 mg human IL-2 and 20 mg L-Cysteine in 1 ml 0.05M phosphate buffer (pH 5) is added. The mixture is emulsified in an ultrasonic bath for 5 minutes at 20° C. (80 kHz frequency).

The emulsion (containing some preformed liposomes and agglomerates) is then concentrated at 20° C. in a vacuum (20 to 30 mm Hg) to give a gel to which is added 2 ml of the buffer solution whilst the mixture is slowly stirred. An aqueous liposomal suspension results.

The liposomes are separated from the non-incorporated active agent by the following steps:

(a) centrifugation (5 minutes, 20°, 5000 G). The non-incorporated active agent remains in the supernatant liquid and the liposome sediment is resuspended.

(b) gel column chromatography as (Biogel A 1.5 or Sephadex G 50). The liposome-containing eluate is concentrated by ultrafiltration or dialysis against a 0.9% brine solution.

The resultant liposomal suspension is lyophilisated.

ANALYSIS

The liposomes are found to incorporate about 50–90% of the human IL-2.

ACTIVITY AND UTILITY

The liposomes are found to show the same order of activity as human IL-2 itself in the above-mentioned bioassay test.

EXAMPLE B2

Preparation of Liposomes 500 mg of lecithin (Epikuron 145 V) are dissolved in 200 ml methylene chloride and placed in a round bottomed flask. An aqueous solution of 0.5 mg human IL-2 and 100 mg L-Cysteine in 10 ml 0.05M phosphate buffer (pH 5) is added. The mixture is emulsified in an ultrasonic bath for 10 minutes at room temperature (20° C.). The resultant emulsion (containing some preformed liposomes and agglomerates) is then concentrated at 35° C. for 10 minutes in a vacuum (20 to 30 mm Hg) to give a gel to which 10 ml of buffer solution is added. The mixture is stirred for 30 minutes at room temperature.

The liposomes are isolated by centrifugation at 150,000 g at 4° C. for 4 hours.

EXAMPLE B3

Preparation of Liposomes

Carried out in analogous manner to Example B2, but concentrating at 80° C. for 5 minutes instead of at 35° C. for 10 minutes. The lecithin used was Soja phosphate NB 95 H. The centrifugation was effected for 2 hours instead of 4 hours.

EXAMPLES B4 and B5

Preparation of Liposomes

Carried out in analogous manner to examples 2 and 3, but without L-Cysteine being present.

ANALYSIS OF LIPOSOMES

Supernatant Liquid

The supernatant liquid after centrifugation is analysed by reversed phase high performance liquid chromatographic techniques as described above and contain less than 10% of the original human IL-2.

Biological activity

The liposomes are analysed according to the series dilution test on the incorporation of $^3$[H]-thyridine in IL-2 dependent CHL-(16) cells in the test described above (S. Gilles et al). The concentration of IL-2 which produces 50% of the maximal growth of $10^4$ cells after 24 hours is measured immediately after preparation (Value A° in mg/ml) and after 2 weeks storage at 4° C. (Value $A^2$ in ng/ml). In this test the substance human IL-2 itself had a value of 0.2 ng/ml.

| Results Example | A° (ng/ml) | $A^2$ (ng/ml) |
|---|---|---|
| B2 | 0.8 | 2.4 |
| B3 | 20.0 | 35.0 |

PROCESS C

EXAMPLE C1

Preparation of Liposomes 50 micromoles of purified lecithin and 50 micromole of cholesterol are dissolved in 20 ml chloroform and evaporated in a rotary evaporator under nitrogen. The residue is taken up in 5 ml diethyl ether. 600 micrograms human IL-2 (as a powder e.g. particle size 5 to 50 microns) are added. To this solution 1.5 ml of 0.05 molar phosphate buffer are added.

The mixture is then irradiated with an ultrasonic probe at 5° C. for 5 minutes to give a homogenisate. The resultant emulsion is concentrated in a rotary evaporator in two stages. In the first stage the pressure is about 400 Torr Hg and maintained until there is a viscous gel. This gel is treated with 1.5 ml 0.05M phosphate buffer (pH 5), and the container shaken slightly to give an aqueous suspension. The aqueous suspension is then subjected to a second evaporation stage at RT and normal pressure for 15 minutes to give a non-transparent suspension of liposomes.

To remove the last traces of organic solvent an ultrafiltration over an ion-exchange column (Sephadex 650) may be carried out.

ANALYSIS OF LIPOSOMES

The liposomes are found to incorporate about 50–90% of the human IL-2.

ACTIVITY AND UTILITY

The liposomes are found to show the same order of activity as human IL-2 itself in the above-mentioned bioassay test.

EXAMPLE C2

Preparation of Liposomes 500 mg of lecithin (EPIKURON 145 V) and 0.5 mg human IL-2 are dissolved in 20 ml methylene chloride. 10 ml 0.05 molar phosphate buffer is added.

The mixture is then irradiated in an ultrasonic bath for 5 minutes at room temperature (ca 20° C.). The resultant emulsion is concentrated in a rotary evaporator at 35° C. for 10 minutes, until there is a viscous gel. 10 ml 0.05M phosphate buffer solution (pH 5) is then added and the container rotated for 30 minutes at room temperature.

The liposomes are isolated by centrifugation at 150,000 g at 4° C. for 4 hours.

EXAMPLE C3

Preparation of Liposomes

Example C4 is repeated with concentration at 80° for 5 minutes instead of 35° C. for 10 minutes. The lecithin was Soja phosphatic NC 95 H. The centrifugation was effected for 2 hours.

ANALYSIS OF LIPOSOMES

Supernatant liquid

The supernatant liquid after centrifugation is analysed by reversed phase high performance liquid chromatography techniques as described above and contain less than 10% of the original human IL-2.

Biological activity

The liposomes are analysed according to the series dilution test on the incorporation of $^3[H]$-thyridine in IL-2 dependent CHLL-(16) cells in the test described above (S. Gilles et al).

The concentration of IL-2 which produces 50% of the maximal growth of $10^4$ cells after 24 hours is measured immediately after preparation (Value A° in ng/ml) and after 2 weeks storage at 4° C. (Value $A^2$ in ng/ml). In this test the substance human IL-2 itself had a value of 0.2 ng/ml.

| Results Example | A° (ng/ml) | $A^2$ (ng/ml) |
|---|---|---|
| C2 | 1.2 | 2.9 |
| C3 | 12.5 | 20.0 |

In any of the above Examples of processes A, B or C the human IL-2 may be replaced by IL-2-serine 125, IL-2 A-1, IL-2 A-2, IL-2 B-1, IL-2 B-2, IL-2 Gln 26, IL-2 Phe-121 or IL-2 Stop 121.

What is claims is:

1. Interleukin-2 containing liposomes.
2. Liposomes according to claim 1 wherein the interleukin is human IL-2.
3. Liposomes according to claim 1 wherein the interleukin is IL-2-serine 125.
4. Liposomes according to claim 1 wherein the interleukin is IL-2 A-1, IL-2 A-2, IL-2 B-1 or IL-2 B-2.
5. Liposomes according to claim 1 wherein the interleukin is IL-2 Gln-26, IL-2 Phe-121 or IL-2 Stop-121.
6. The liposomes of claim 1 in which the lipid content consists essentially of phospholipids.
7. The liposomes of claim 1 in which the lipid content consists essentially of phospholipids and steroid lipids in a weight ratio of phospholipids to steroid lipids of from 6:1 to 1:1.
8. The liposomes of claim 1 in which the interleukin-2 is present in an amount of 20 to 200 micrograms per milliliter of the aqueous phase and the lipid concentration is present in an amount of 10 to 100 milligrams per milliliter of the aqueous phase.
9. Lyophilized interleuken-2 containing liposomes.
10. The liposomes of claim 2 in which the lipid content consists essentially of phospholipids.
11. The liposomes of claim 2 in which the lipid content consists essentially of phospholipids and steroid lipids in a weight ratio of phospholipids to steroid lipids of from 6:1 to 1:1.
12. The liposomes of claim 2 in which the interleukin-2 is present in an amount of 20 to 200 micrograms per milliliter of the aqueous phase and the lipid concentration is present in an amount of 10 to 100 milligrams per milliliter of the aqueous phase.
13. Lyophilized human interleukin-2 containing liposomes.
14. The method of stimulating the T-cell dependent immune response in a mammal in need of such treatment comprising intravenously administering to such mammal a T-cell dependent immune response stimulating effective amount of interleukin-2-containing liposomes.
15. The method of claim 14 in which the interleukin-2-containing liposomes are human interleukin-2-containing liposomes.

* * * * *